United States Patent [19]

Park et al.

[11] Patent Number: 5,091,602
[45] Date of Patent: Feb. 25, 1992

[54] PROCESS FOR PREPARING 1,1,1-TRIFLUORO-2,2-DICHLOROETHANE

[75] Inventors: Kun Y. Park; Hoon S. Kim, both of Seoul, Rep. of Korea

[73] Assignee: Korea Institute of Science and Technology, Seoul, Rep. of Korea

[21] Appl. No.: 647,568

[22] Filed: Jan. 28, 1991

[30] Foreign Application Priority Data

Oct. 18, 1990 [KR] Rep. of Korea .............. 16639/1990

[51] Int. Cl.$^5$ .............................................. C07C 17/08
[52] U.S. Cl. ........................................................ 570/167
[58] Field of Search ............................................ 570/167

[56] References Cited

U.S. PATENT DOCUMENTS 2,927,948  3/1960  Scherer et al. .................. 570/167

Primary Examiner—Alan Siegel
Attorney, Agent, or Firm—Leydig, Voit & Mayer

[57] ABSTRACT

A process is provided for producing 1,1,1-trifluoro-2,2-dichloroethane of formula (I) wherein pentachloroethane of formula (II) is reacted with hydrofluoric acid in the presence of a mixed catalyst either of pentahaloantimony of general formula (III) and $MX_2L_2$ of general formula (IV) or of pentahaloantimony of general formula (III) and $MX_2(L-L)$ of general formula (V)

| | |
|---|---|
| $CF_3CHCl_2$ | (I) |
| $CCl_3CHCl_2$ | (II) |
| $SbX_5$ | (III) |
| $MX_2L_2$ | (IV) |
| $MX_2(L-L)$ | (V) | wherein,
  X is a chloro or bromo group,
  M is nickel, palladium or platinum,
  L is represented by $PR_3$ in which R is phenyl, methyl, ethyl, iso-propyl, n-butyl or tert-butyl and L—L is 1,2-bis (diphenylphosphino) ethane (DIPOS), 1,2-diaminoethane or $S_2CH_2$.

7 Claims, No Drawings

PROCESS FOR PREPARING 1,1,1-TRIFLUORO-2,2-DICHLOROETHANE

BACKGROUND OF THE INVENTION

This invention relates to the novel and improved process for preparing 1,1,1-trifluoro-2,2-dichloroethane represented by the following formula (I);

$$CF_3CHCl_2 \quad (I)$$

The compound of formula (I) may be a prospective compound as an alternative of chlorofluorocarbon (CFC), which has a direct influence on the environmental pollution, the compound of formula (I) has a minimal destructive effect on the ozone layer. In addition, the compound may be used widely as foaming agent, coolant and detergent.

SUMMARY OF THE INVENTION

The process for preparation in the present invention is summarized as follows.

1,1,1-trifluoro-2,2-dichloroethane of formula (I) is prepared by reacting pentachloroethane of formula (II) with hydrofluoric acid in the presence of a catalyst.

$$CCl_3CHCl_2 \quad (II)$$

The known processes for preparing the compound of formula (I) are disclosed in many literatures; for example, in U.S. Pat. No. 4,060,469 is described a process for producing the compound of formula (I) by photoreacting 1,1,1-trifluoro-2-chloroethane with chlorine. However, this process is not desirable in industrialization due to complicated equipments, etc. Also, U.S. Pat. No. 2,927,948 discloses that the compound of formula (I) is prepared by reacting pentachloroethane of formula (II) with hydrofluoric acid in the presence of trifluoroantimony ($SbF_3$) catalyst. However, the employed catalyst, $SbF_3$ has such a low solubility that the pressure and temperature of the reaction must be elevated and that the yield is considered low. In addition, in U.S. Pat. No. 3,258,500, though HCFC-123 is prepared by reacting tetrachloroethylene with hydrofluoric acid using chromium or aluminum based catalyst, this process leads to high reaction temperature, mass-production of by products and rapid decrease of catalyst activity.

The inventors have found that when pentahaloantimony catalyst is used in fluorination of pentachloroethane of formula (II), the rate of the reaction considerably decreases by conversion of pentahaloantimony into a stable and nearly insoluble compound, $SbF_3$ as the reaction proceeds.

Accordingly, it has been found that large quantities of chlorine are required to reactivate the catalyst; and the excessive chlorine used is reacted with the intermediate unsaturated compounds produced in the process of dehydrochlorination and this leads to a production of unnecessary byproducts such as CFC-112, CFC-113 and the like.

DETAILED DESCRIPTION OF THE INVENTION

It is a primary object of a invention to provide an improved process for preparing the compound of formula (I) which addressed the problems associated with known processes. More specifically, 1,1,1-trifluoro-2,2-dichloroethane of formula (I) was conveniently prepared by reacting pentachloroethane of formula (II) with hydrofluoric acid in the presence of a catalyst. This catalyst is defined as, an organometallic compound consisting of either pentahaloantimony of general formula (III) and $MX_2L_2$ of general formula (IV) or pentahaloantimony of general formula (III) and $MX_2(L—L)$ of general formula (V).

| | |
|---|---|
| $SbX_5$ | (III) |
| $MX_2L_2$ | (IV) |
| $MX_2(L—L)$ | (V) | wherein,
X is a chloro or bromo group,
M is nickel, palladium or platinum,
L is a phosphine compound represented by $PR_3$ (wherein R is phenyl, methyl, ethyl, iso-propyl, n-butyl or ter-butyl), and L—L is 1,2 bis (diphenylphosphino) ethane (DIPOS), 1,2-diaminoethane (en) or $S_2CH_2$.

The amount of pentahaloantimony catalyst used in this invention is 0.3 to 30 moles, and preferably 5 to 10 moles, based on 100 moles of pentahalochloroethane. The organometallic compound of general formula (IV) or of general formula (V) is added as a cocatalyst in an amount of 0.01–0.1 moles per mole of pentahaloantimony.

The reaction is carried out at a temperature from 80° to 180° C., more preferably from 100° to 140° C., by batch or continuous process system. The reaction pressure is preferably 3 to 30 atm, more preferably 8 to 25 atm, and can be appropriately controlled by using back-pressure regulator. Also, outflow of partially fluorinated 1,1-difluoro-1,2,2-trichloroethane was inhibited by attaching a column to the upper part of the reactor. In the continuous process system, 1,1,1-trifluoro-2,2-dichloroethane is successively collected and 1,1-difluoro-1,2,2-trichloroethane is recycled to the reactor.

The recovered 1,1,1-trifluoro-2,2-dichloroethane was washed with an alkaline aqueous solution, e.g. aqueous solution of sodium hydroxide or magnesium oxide and subsequently with water, passed through a column of calcium chloride to remove water and collected at −20° C.

As mentioned above, the subject invention is characterized in that by using an organometallic compound as a cocatalyst which is soluble in the reaction media, the speed of fluorination is considerably increased, the reaction is proceeds uniformly, and the reaction operation and the temperature control can be conveniently adjusted. In addition, excessive chlorine is not required to maintain the activity of catalyst and the generation of by-products can be remarkably reduced.

The following examples are given by way of illustration and are not to be construed as in any way limiting the scope of the invention.

EXAMPLE 1

$SbCl_5$ (10 g), $NiCl_2$ $(PEt_3)_2$, (1.5 g), pentachloroethane (100 g) and hydrofluoric acid (50 g) are successively introduced into a 1000 ml high-pressure reactor equipped with a stirrer. The reactants were heated to a temperature of 130° C. while stirred at the rate of about 1900 rpm. When the pressure of the reactor reached 20 atm, HF was introduced again at the rate of 1 g/min.

After the reaction mixture was reacted for one hour with the pressure of the reactor maintained at 20 atm by means of pressure-controlling valve attached to the outlet of the reactor, the reaction product was analyzed by gas chromatography. The results were as follows.

| pentachloroethane | 0.1 mole % or less |
|---|---|
| 1,1,1-trifluoro-2,2-dichloroethane | 33 mole % |
| 1,1-difluoro-1,2,2-trichloroethane | 14 mole % |
| 1,1,2-trifluoro-1,2,2-trichloroethane | 3 mole % |

EXAMPLE 2

After the reaction was completed in example 1 and HF and organic compounds except the catalyst were removed from the reactor, pentachloroethane (100 g) and hydrofluoric acid (50 g) were introduced into the reactor and reacted in the same condition as described in Example 1.

After one hour, the results of analyzing the products were as follows.

| pentachloroethane | 0.1 mole % or less |
|---|---|
| 1,1,1-trifluoro-2,2-dichloroethane | 81 mole % |
| 1,1-difluoro-1,2,2-trichloroethane | 16 mole % |
| 1,1,2-trifluoro-1,2,2-trichloroethane | 1 mole % |
| 1-fluoro-1,1,2,2-tetrachloroethane | 2 mole % |

EXAMPLES 3-8

These tests were carried out varying the kinds of organometallic compounds under the same conditions as Example 1. The results are listed in Table 1. The amount used organometallic compounds used was 0.0041 moles, the same amount as in Example 1.

What is claimed is:

1. A process for preparing 1,1,1-trifluoro-2,2-dichloroethane of formula I ($CH_3CHCl_2$), comprising reacting pentachloroethane of formula II ($CCl_3CHCl_2$) with hydrofluoric acid in the presence of a catalyst system consisting of either pentahaloantimony of formula III ($SbX_5$) and a compound of formula IV ($MX_2L_2$) or pentahaloantimony of formula III ($SbX_5$) and a compound of formula V ($MX_2(L-L)$), wherein X is a chloro or bromo group; M is nickel, palladium, or platinum; L is $PR_3$ wherein R is a phenyl, methyl, ethyl, isopropyl, n-butyl, or terbutyl group; and L—L is 1,2-bis(diphenyl phosphino)ethane, 1,2-diaminoethane, or $S_2CH_2$.

2. The process according to claim 1, wherein the concentration of pentahaloantimony of general formula III added as the catalyst is about 5 to about 10 moles based on 100 moles of pentachloroethane.

3. The process according to claim 1, wherein the amount of catalyst of formula IV or formula V added as a cocatalyst is about 0.01 to about 0.1 moles per mole of pentahaloantimony.

4. The process according to claim 1, wherein the reaction is carried out at a temperature of from about 100° C. to about 140° C.

5. The process according to claim 1, wherein the reaction is carried out at a pressure of from about 8 to about 25 atm.

6. The process according to claim 1, wherein the molar ratio of hydrofluoric acid to pentachloroethane is about 3 to about 10.

7. The process according to claim 4, wherein the reaction is carried out at a pressure of from about 8 to about 25 atms.

TABLE 1

| Example No. | Kinds of organo-metallic compound | composition of the products (mole %) | | | | |
|---|---|---|---|---|---|---|
| | | $CCl_3CHCl_2$ | $CF_3CHCl_2$ | $CF_2ClCHCl_2$ | $CF_2ClFCl_2$ | others |
| 3 | $NiCl_2(PPh_3)_2$ | 0.1 or less | 78 | 17 | 3 | 2 |
| 4 | $NiCl_2(PBu_3)_2$ | " | 79 | 18 | 2 | 1 |
| 5 | $NiCl_2(DIPOS)$ | " | 83 | 15 | 1 | 1 |
| 6 | $PdCl_2(PEt_3)_2$ | " | 90 | 9 | 1 | 0 |
| 7 | $PdCl_2(PPh_3)_2$ | " | 88 | 9 | 1 | 2 |
| 8 | $NiCl_2(S_2CH_2)$ | " | 80 | 16 | 2 | 2 |

[The abbreviations used in Table 1 have the following meanings; Ph: phenyl, Bu: butyl, Et: ethyl]